US008460352B2

(12) United States Patent
DeMore et al.

(10) Patent No.: US 8,460,352 B2
(45) Date of Patent: Jun. 11, 2013

(54) SITE-SPECIFIC PAD WITH NOTCH

(75) Inventors: Anthony DeMore, Chardon, OH (US);
Andrew P. Howansky, Copake Falls, NY (US); Christopher S. Kanel, Hudson, NY (US); Stephen Russak, Demarest, NJ (US); John D'Aponte, Brooklyn, NY (US)

(73) Assignee: Kaz USA, Inc., Southborough, MA (US)

( * ) Notice: Subject to any disclaimer, the term of this patent is extended or adjusted under 35 U.S.C. 154(b) by 1185 days.

(21) Appl. No.: 11/428,723

(22) Filed: Jul. 5, 2006

(65) Prior Publication Data
US 2008/0009926 A1    Jan. 10, 2008

(51) Int. Cl.
*A61F 7/00*    (2006.01)
(52) U.S. Cl.
USPC .............................. 607/96; 607/108; 607/112
(58) Field of Classification Search
USPC ................. 606/27–31; 219/600, 601; 607/96, 607/98, 99, 108–112
See application file for complete search history.

(56) References Cited

U.S. PATENT DOCUMENTS

| 4,081,150 A * | 3/1978 | Tyson ........................... 607/112 |
| 4,372,318 A | 2/1983 | Viesturs |
| 5,062,414 A * | 11/1991 | Grim ............................... 602/19 |
| 5,398,667 A | 3/1995 | Witt |
| 6,860,896 B2 * | 3/2005 | Leber et al. ....................... 607/1 |
| 2006/0089582 A1 | 4/2006 | Rakhmanin |

FOREIGN PATENT DOCUMENTS

| GB | 2302651 A | 1/1997 |
| WO | WO 94/00087 A1 | 1/1994 |

OTHER PUBLICATIONS

Extended European Search Report for EP 07799312.9 dated Oct. 18, 2010.

* cited by examiner

*Primary Examiner* — Ahmed Farah
(74) *Attorney, Agent, or Firm* — Stroock & Stroock & Lavan LLP

(57) ABSTRACT

A temperature therapy pad for use with a person including a thermal unit for making the pad either hot or cold and a therapeutic slot extending from one side of the pad which substantially divides the pad into sections. An elastic member may extend across the slot. The therapy pad can include a strap or an adhesive for attaching the therapy pad to a user's body. The thermal unit can be an electric heating coil and include a controller. The thermal unit may also be a material which has a high specific heat capacity or a material which heats when exposed to oxygen. The thermal unit may also be in the form of two separate chemical substances which change temperature when mixed. Another embodiment is for a temperature therapy pad including a substance which presents a heating or cooling sensation to a user's skin.

10 Claims, 5 Drawing Sheets

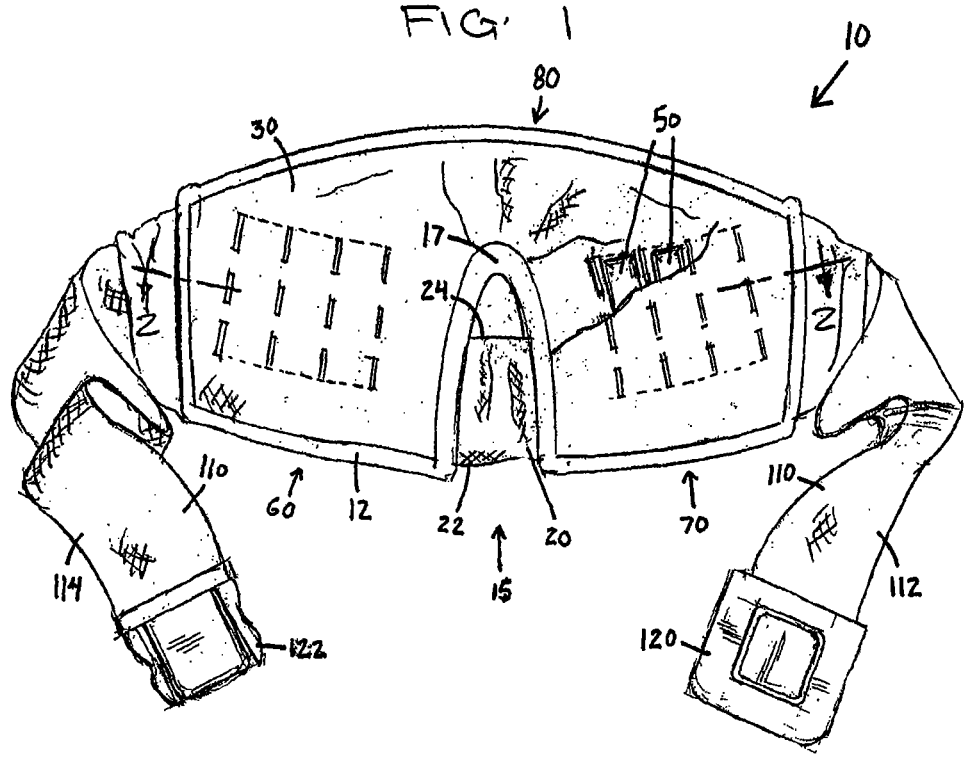
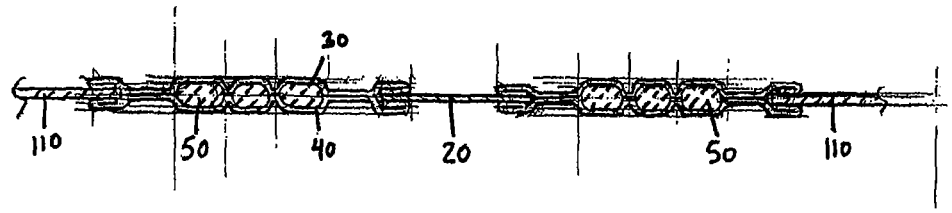
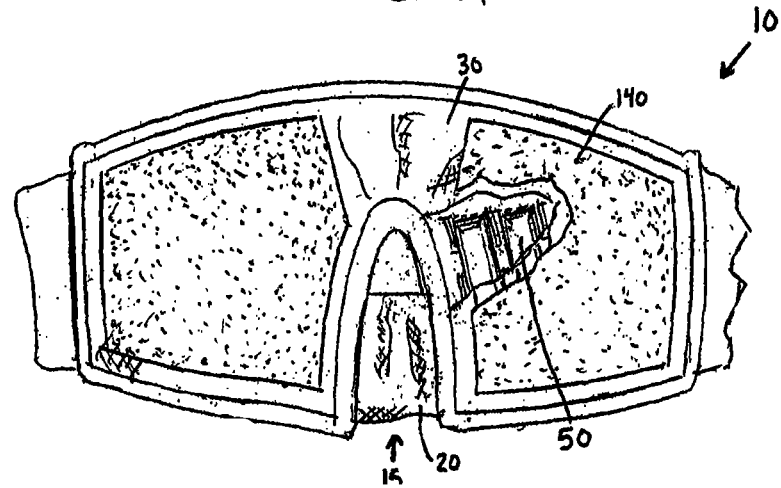

SITE-SPECIFIC PAD WITH NOTCH

FIELD OF THE INVENTION

The invention generally relates to temperature therapy for pain or injuries and specifically relates to a site-specific temperature therapy pad.

BACKGROUND OF THE INVENTION

The administration of temperature therapy and its benefits are well known. The application of heat helps ease pain by stimulating thermoreceptors which reduce pain signals that are sent to the brain. Consequently, muscle discomfort or injury are typically treated with the application of heat. Another benefit of heat is that it increases blood flow allowing muscles to relax and decrease in stiffness. Aside from muscle soreness, heat can also be used to treat joint pain which may be caused by osteoarthritis. The application of heat is also known to treat pain associated with menstrual cramping. On the other hand, impact injuries and joint sprains are frequently treated with the application of a cold substance, such as ice or a chilled liquid or gel. The cold helps reduce swelling and simultaneously relieves pain.

Traditional methods of employing temperature therapy include simple remedies such as hot showers, hot water bottles and electric blankets when heat is needed. Cold therapy can be applied using bags of ice. All of these methods have obvious disadvantages. The heat remedies are rarely available and are not effective for treating a specific body part. On the other hand, ice is temporary in that it melts and a user must "refill" the ice.

Other, more advanced methods of administrating temperature therapy have also been developed. Portable and disposable products have been introduced which can be activated at any time becoming very hot and others very cold. Materials have been developed which can retain their temperature for extended lengths of time supplying continuous temperature therapy. In recent years, wearable temperature therapy pads have been developed allowing a user to administer temperature therapy while remaining active and without continuously supporting the temperature therapeutic device.

The temperature therapy products currently available are well made with respect to their ability to supply heat or cold but they are not designed to conform well with the user's body. This results in much of the heat or cold produced by these products being wasted or misdirected. The present invention is directed to a site-specific wearable temperature therapy pad which is designed to conform to and allow flexibility against the user's body.

SUMMARY OF THE INVENTION

The present invention is for a wearable site-specific temperature therapy pad which provides pain relief and has greater conformability to the user's body and more flexibility with the user's muscles than conventional temperature therapy pads. The temperature therapy pad includes at least one layer of cloth-like material and an outer edge defined by the cloth-like material. The temperature therapy pad also includes a therapeutic slot in the form of a cut-out section extending inward from the edge. The therapeutic slot substantially divides the temperature therapy pad into first and second sections connected by a middle section next to the slot.

The therapeutic slot provides a distinct advantage for the temperature therapy pad of the present invention over conventional temperature pads in that it allows the therapy pad to fit various body types and to continuously target separate muscles or different sides of a joint. For example, the first section may be applied to a first muscle and the second section may be applied to a second muscle. If the user is a larger person the first section and second section may be kept apart by applying the therapy pad to the user with the therapeutic slot in a substantially open position. Alternatively, a smaller person may wear the therapy pad with the therapeutic slot in a substantially closed position with the first section and second section closer together. Further, the therapeutic slot allows the first section and second section to separate and move towards each other with the separate muscles as the user moves.

The therapeutic slot can extend from the edge at least halfway across the temperature therapy pad. The therapeutic slot may be substantially V-shaped such that there is a slight gap between the sections of the therapy pad when it is in a relaxed state. The apex of the therapeutic slot, positioned next to the middle section, may be rounded or pointed.

One embodiment of the site-specific temperature therapy pad of the present invention includes an inner layer which contacts a user and an outer layer which is exposed to the air. The inner layer and outer layer may be formed of a fabric, plastic or any cloth-like material and can be made of differing materials to each other. One or more thermal units are disposed between the inner and outer layers. The thermal units may be intended for heat therapy and be hotter than ambient temperature or they may be intended for cold therapy and can be cooler than ambient temperature.

The therapy pad can be provided with one or more flexible members, in the area of the therapeutic slot. The flexible member may be formed of any flexible cloth-like material, such as elastic. In situations where the therapy pad is being held in tension such that the therapeutic slot is substantially open, the elastic member helps contract the therapeutic slot after the tension is released and move the sections of the therapy pad closer together.

The therapy pad with the therapeutic slot may be designed for various parts of the body. The therapeutic slot provides increased flexibility of the therapy pad and allows for a better fit of the therapy pad to a variety of body parts including the lower back, abdomen, neck, shoulders, knees, ankles, elbows and wrists.

Various methods may be used to attach the therapy pad to the user. The therapy pad may include at least one strap which can be wrapped around the appropriate body part to attach the therapy pad to the user. The strap may be either elastic or inelastic. Attachment members may be included for securing the strap to the user. The strap may be formed as a single piece or in sections.

An alternative method of attaching the therapy pad to the user is by using an adhesive disposed on an inner surface of the inner layer of the pad. In this case, the therapy pad does not require a strap, but one may be provided for extra stability. The therapeutic slot is especially advantageous for embodiments including an adhesive. As the user moves and bends, his skin stretches and contracts; this is especially true around joints. The therapeutic slot allows the first and second section to separate and come together as the user's skin stretches and contracts, respectively.

A variety of different types of thermal units may be included in the therapy pad. The types of thermal units may be separated into two major categories: electrical and non-electrical.

An electrical embodiment of the temperature therapy pad includes an electrical heating coil, which gets hot as current flows through it. The heating coil is disposed between the inner layer and outer layer. To increase the effective heating area of the therapy pad the electric heating coil may wind back and forth through the therapy pad.

Current may be supplied to the electrical heating coil through a wire. The origin of the current may be a battery or a power outlet. A control unit may be provided along the wire or within the therapy pad to control the amount or location of the heat provided by the therapy pad.

It may be desirable to reduce the heat emitted from the middle section of the therapy pad. Therefore, one embodiment is a therapy pad which includes insulation surrounding the heating coil within the middle section. Alternatively, at least one heating coil may be provided in each of the first and second section with no heating coil provided in the middle section.

There are various alternatives to using an electrical heating coil which may serve as the thermal unit. The non-electrical options for the thermal unit do not require that the therapy pad include a battery or that it be tethered to an outlet. The non-electrical thermal units may be made of a material which heats when exposed to air, a material with a high specific heat capacity or two different chemicals which change temperature when mixed.

One embodiment of the therapy pad includes at least one thermal unit which is permanently enclosed within the therapy pad. A different embodiment includes a thermal unit which is a removable insert. The use of removable inserts provides distinct advantages over permanent thermal units. If the thermal units are one-time use only, the use of removable inserts prevents the user from having to dispose of the therapy pad entirely after only a single use. Furthermore, removable inserts may be removed once they have reached ambient temperature and new inserts may be added to bring the therapy pad back to a hot or cold temperature.

One embodiment of the non-electrical thermal units may be formed of a material which heats up when exposed to air. Certain mixtures of natural chemicals undergo an exothermic reaction when mixed with oxygen. The thermal unit may be formed by any of such mixtures to provide a therapy pad which produces long-lasting heat. The thermal units using these chemicals are one-time use only. For this reason, therapy pads employing this type of thermal unit may be disposable or may include a disposable insert.

Another embodiment of the thermal units includes a material having a high specific heat capacity. High specific heat capacity thermal units may be designed to emit hot, cold or both hot and cold. Before using the therapy pad the user may prepare the temperature of the high specific heat capacity thermal units. This may be done by a plurality of methods including microwaving the thermal units or placing them in hot water, the refrigerator or the freezer.

Yet another embodiment of non-electrical thermal units include two separate chemical mixtures. Typically one of the chemicals is contained within a breakable pouch. Before using the therapy pad the user breaks the pouch allowing the chemicals to mix. The mixing of the two chemicals results in one of an endothermic or an exothermic reaction making the therapy pad cold or hot, respectively. The thermal units of this variety can be used only one time. Again, the therapy pad may be disposable or the thermal units may be disposable.

The temperature therapy pad may include more than one type of thermal unit. A high specific heat capacity thermal units may used in combination with an electrical heating coil. As current passes through the coil it rises in temperature and heats the high specific heat capacity thermal unit. After the current is stopped, the temperature therapy pad may retain its heat for long periods of time due to the high specific heat capacity thermal unit.

A different embodiment of the therapy pad is pharmacological. The therapy pad with the therapeutic slot may include a single layer with an inner surface coated with a liquid or paste. The liquid provides a sense of either heating or cooling using well known substances such as menthol or trolamine salicylate. Additionally, the inner surface can be porous to absorb the liquid and release specific quantities over time to allow for extended treatment. Alternatively, an inner layer can be porous and removable units, placed inside the therapy pad, can contain the liquid to be slowly dispensed through the inner layer. The pharmacological therapy pad may also include adhesive such that a strap or belt is not required.

BRIEF DESCRIPTION OF THE DRAWINGS

These and other objects and features of the invention will become more apparent by referring to the drawings, in which:

FIG. 1 is a front view of the site-specific temperature therapy pad including an attachment strap in accordance with the claimed invention;

FIG. 2 is a cross-section view of the therapy pad shown in FIG. 1 taken along line 2-2;

FIG. 4 is a front view of an alternative embodiment of the therapy pad;

DETAILED DESCRIPTION OF THE PREFERRED EMBODIMENTS

Figure 3:
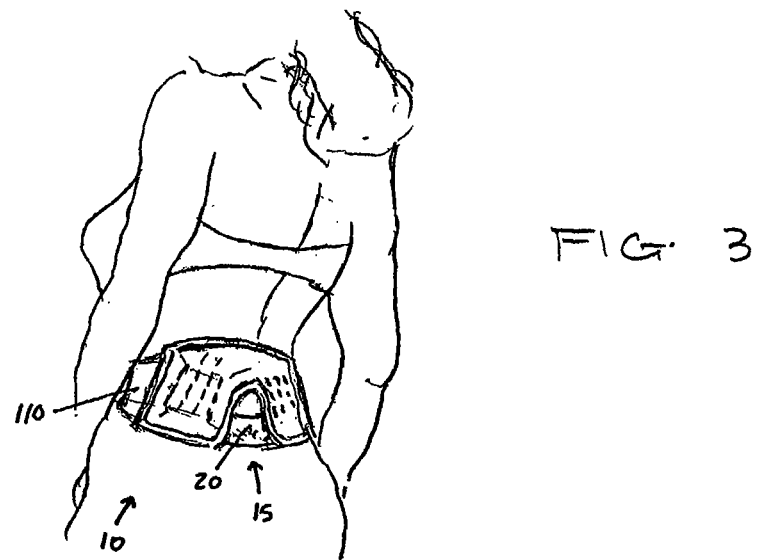
FIG. 3 is a temperature therapy pad in accordance with the present invention shown on the lower back of a person.

The site-specific temperature therapy pad 10 according to one embodiment of the present invention is shown in FIGS. 1 and 2. Therapy pad 10 includes an inner layer 30 which contacts a user and outer layer 40 which is exposed to the air. Inner layer 30 and outer layer 40 may be formed of a fabric, plastic or any cloth-like material and can be made of differing materials to each other. One or more thermal units 50 are disposed between inner layer 30 and outer layer 40. Therapy pad 10 also includes therapeutic slot 15, a cut-out section extending inward from edge 12 of the therapy pad 10. Therapeutic slot 15 substantially divides therapy pad 10 into two parts, namely, first section 60 and second section 70 which are connected by middle section 80. Therapy pad 10 is designed such that it may be worn by a user allowing the user to remain active without having to hold the therapy pad.

Therapeutic slot 15 provides a distinct advantage to therapy pad 10 over conventional temperature pads in that it allows therapy pad 10 to fit various body types and to continuously target separate muscles or different sides of a joint. For example, first section 60 may be applied to a first muscle and second section 70 may be applied to a second muscle. If the user is a larger person, first section 60 and second section 70 may be kept apart by applying therapy pad 10 with therapeutic slot 15 in a substantially open position. Alternatively, a smaller person may wear therapy pad 10 with therapeutic slot 15 in a substantially closed position with first section 60 and second section 70 closer together. Further, therapeutic slot 15 allows first section 60 and second section 70 to separate and move toward each other with the first and second muscle as the user moves. If the first and second muscles move closer, therapeutic slot 15 may close. Likewise, if the first and second muscles move apart, therapeutic slot 15 may open.

Therapeutic slot 15 can extend from edge 12 at least halfway across temperature pad 10. Therapeutic slot 15 may be substantially V-shaped allowing first section 60 and second section 70 to have a slight gap therebetween when therapy pad 10 is in a normal and relaxed state. Apex 17, positioned at the inner end of therapeutic slot 15 next to middle section 80, may be rounded as shown in FIG. 1 or pointed.

Therapy pad 10 can be provided with one or more flexible members 20, spanning therapeutic slot 15. The flexible members 20 may be formed of stretchable fabric, flexible plastic or elastic. Alternatively, the flexible members may be formed by a spring or spring-like material covered by cloth. In situations where therapy pad 10 is being held in tension such that therapeutic slot 15 is substantially open and first section 60 is separated from second section 70, flexible member 20 helps contract therapeutic slot 15 after the tension is released. Flexible member 20 may be arranged such that its outer edge 22 is either relatively flush with edge 12 of therapy pad 10 as shown in FIG. 1 or so that it is removed from edge 12 and held further back in therapeutic slot 15. Additionally, inner edge 24 may be positioned away from apex 17 as shown in FIG. 1 such that a gap is formed in therapy pad 10 near apex 17. Alternatively, flexible member 20 may extend up to apex 17 such that flexible member 20 does not have an inner edge. In another embodiment, flexible member 20 is omitted entirely.

Therapy pad 10 with therapeutic slot 15 may be designed for various parts of the body. Therapeutic slot 15 provides increased flexibility of therapy pad 10 and allows for a better fit of therapy pad 10 to a variety of body parts including the lower back, abdomen, neck, shoulders, knees, ankles, elbows and wrists.

As shown in FIG. 3, therapy pad 10 may be designed specifically for a person's lower back. In one embodiment, therapy pad 10 is designed such that a first section 60 is worn on a right side of the user's lower back while a second section 70 is worn on a left side of the user's lower back. Therapeutic slot 15 and middle section 80 are each arranged over the user's spine, preferably with therapeutic slot 15 below middle section 80. If the user is a large person, he may wear therapy pad 10 in tension such that therapeutic slot 15 is open and the user's lower back muscles are covered by therapy pad 10 even at their outer extremities. In contrast, if the user is a small person he may wear therapy pad 10 with therapeutic slot 15 substantially closed so that even close to the user's spine his lower back muscles are still covered by therapy pad 10. In addition, first section 60 and second section 70 move with the user's back muscles as a result of therapeutic slot 15. For instance, if the user is arching backwards his lower back muscles will be very close together, as will first section 60 and second section 70. If the user proceeds to bend down and roll his back over, the lower back muscles will separate. Therapeutic slot 15 allows first section 60 and second section 70 to subsequently separate allowing thermal units 50 to continuously target those muscles.

In one embodiment, a plurality of thermal units 50 or a single thermal unit 50 may supply heat or cold throughout therapy pad 10. Alternatively, any section of thermal unit 50 which is disposed within middle section 80 may be insulated such that the user's spine is not subjected to the strong temperature of thermal units 50. In a preferred embodiment, first section 60 and second section 70 may each have at least one thermal unit 50 and middle section 80 may contain no thermal unit. This prevents the user's spinal cord from being subjected to either the hot or cold of thermal units 50.

Another embodiment of therapy pad 10 is designed for the neck and shoulders. Again middle section 80 and therapeutic slot 15 are placed over the spinal cord with first section 60 worn over one side of the neck and one shoulder and second section 70 is worn over the other side of the neck and the other shoulder. If the user rolls his shoulders up and back his right and left upper trapeziuses will come together. The first section 60 and the second section 70 will subsequently also come together, thereby continuously targeting the desired muscles. As the user rolls his shoulders down and forward the first section 60 and second section 70 will spread apart along with the user's right and left upper trapeziuses.

Therapy pad 10 may also be designed for use with joints. One embodiment of therapy pad 10 is designed specifically for use with a person's knee. Therapy pad 10 may be worn such that first section 60 and second section 70 may each be positioned on opposite sides of the user's knee with therapeutic slot 15 placed over the user's kneecap. Therapeutic slot 15 allows first section 60 and second section 70 to move outward as the user bends his knee, keeping therapy pad 10 and thermal units 50 contained therein close to the joint.

Other embodiments of the claimed invention include designs for various joints and body parts. Joint designs include embodiments for the shoulder, elbow, ankle and wrist. Another embodiment is for a therapy pad designed for the lower abdomen for the relief of menstrual cramping. Other embodiments also include designs for the middle back and neck.

Various methods may be used to attach therapy pad 10 to the user. Therapy pad 10 may include at least one strap which can be wrapped around the appropriate body part to attach therapy pad 10 to the user. For example, embodiments for the back or abdomen may include a belt 110 as shown in FIGS. 1-3. Belt 110 may be either inelastic or elastic such that belt 110 is flexible and stretchable allowing therapy pad 10 to be worn by people of varying size. Attachment members 120 and 122 may be included for securing belt 110 to the user. Belt 110 may be formed of segments 112 and 114 extending from opposite sides of therapy pad 10 and each containing at least one attachment member 120 and 122 respectively. The belt may be secured by fastening attachment member 120 of belt segment 112 to the opposing attachment member 122 of belt segment 114. Alternatively, belt 110 may be a single piece with attachment member 120 located on an end of belt 110 and opposing attachment member 122 located on the end of therapy pad 10 that is opposite belt 110. Attachment members 120 and 122 may be any appropriate means for securing a belt or strap including a latch, button, hook, buckle, zipper and/or Velcro®. In another embodiment a flexible strap may be attached to two opposing ends of therapy pad 10 forming a ring-type structure. This embodiment requires that the user place therapy pad 10 over an extremity and pull therapy pad 10 into place.

An alternative method of attaching therapy pad 10 to the user is by using an adhesive 140. The embodiment shown in FIG. 4 includes inner layer 30 of therapy pad 10 covered with a layer of adhesive 140. In this case, therapy pad 10 does not require a strap, but one may be provided for extra stability. Therapeutic slot 15 is especially advantageous for embodiments including adhesive 140. As the user moves and bends, his skin stretches and contracts; this is especially true around joints. Therapeutic slot 15 allows first section 60 and second section 70 to separate and come together as the user's skin stretches and contracts, respectively. If therapeutic slot 15 were not included on therapy pad 10 the user would have limited motion. If the user stretched too far, the therapy pad without the therapeutic slot would be ripped from the user's skin resulting in discomfort to the user.

A variety of types of thermal units 50 may be included in therapy pad 10. The types of thermal units 50 may be separated into two major categories: electrical and non-electrical.

Figure 5:
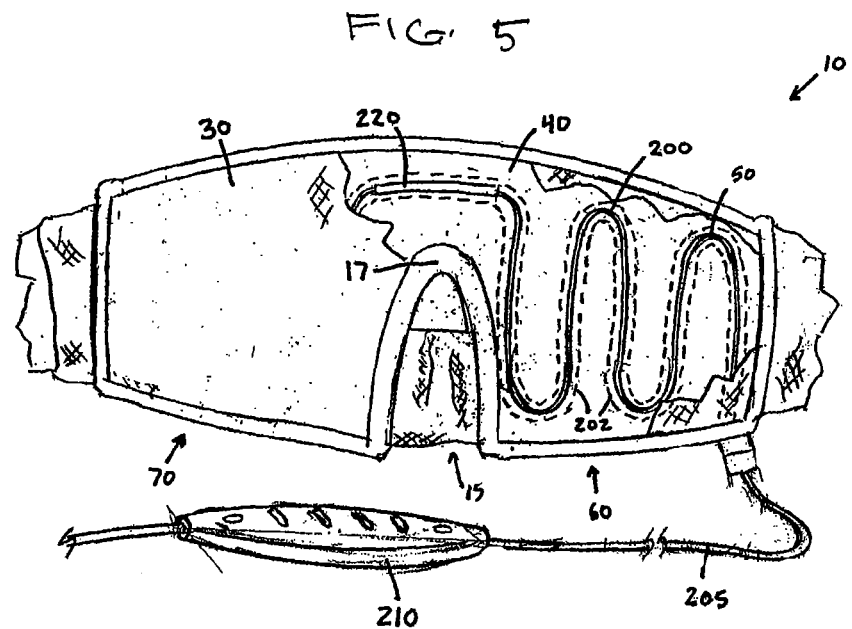
FIG. 5 is a front and partial cut-away view of a therapy pad including an electrical thermal unit.

FIG. 5 shows a therapy pad 10 including an electrical heating coil 200, which gets hot as current flows through it. Electrical heating coil 200 may be formed of any metal or other material that is appropriate and known in the art. Electrical heating coil 200 is disposed between inner layer 30 and outer layer 40. To increase the effective heating area of therapy pad 10 the electric heating coil 200 may wind back and forth through therapy pad 10 as shown in FIG. 5. Inner layer 30 may be attached to outer layer 40 in areas around electrical heating coil 200 to secure it in place. For example inner layer 30 may be stitched to outer layer 40 such that the stitches 202 prevent electrical heating coil 200 from moving out of place.

Current may be supplied to electrical heating coil 200 through wire 205. The origin of the current (not shown) may be a battery or a power outlet. A portable embodiment of temperature therapy pad 10 may be powered by a battery or a number of batteries. Temperature therapy pad 10 may include a pocket or holder to store the batteries while therapy pad 10 is in use. The portable therapy pad 10 may also be operable for use in a vehicle. For instance, wire 205 may include a plug or may be fit with an adapter for receiving current from the cigarette lighter of a car.

A control unit 210 may be provided along wire 205 or within therapy pad 10 to control the amount or location of the heat provided by therapy pad 10. Control unit 210 may be designed to allow the user to increase or decrease the amount of current flowing through electrical heating coil 200. Alternatively, therapy pad 10 may include a plurality of heating coils 200 and the control unit 210 may be designed to allow the user to selectively turn on as many of the heating coils as desired. If each heating coil 200 is spread throughout therapy pad 10, activating more of the heating coils 200 makes therapy pad 10 hotter. On the other hand, if each heating coil 200 is provided in a different section of therapy pad 10 the user may control the location of the heat emitted by therapy pad 10 by controlling the heating coil(s) 200.

As mentioned above, it may be desirable to reduce the heat emitted from middle section 80 of therapy pad 10. Therefore, the embodiment shown in FIG. 5 is a therapy pad 10 which includes insulation 220 surrounding heating coil 200 within middle section 80. Alternatively, at least one heating coil 200 may be provided in each of first section 60 and second section 70. Heating coils 200 within first section 60 may be connected to heating coils 200 within second section 70 by means of conductive wires which do not produce significant amounts of heat.

There are various alternatives to electrical heating coil 200 which may serve as thermal unit 50. The non-electrical options of thermal unit 50 do not require that therapy pad 10 include a battery or that it be tethered to an outlet. The non-electrical thermal units 50 may be made of a material which heats when exposed to air, a material with a high specific heat capacity or two different chemicals which change temperature when mixed. Embodiments with all of these options are discussed in greater detail below.

Figure 6:
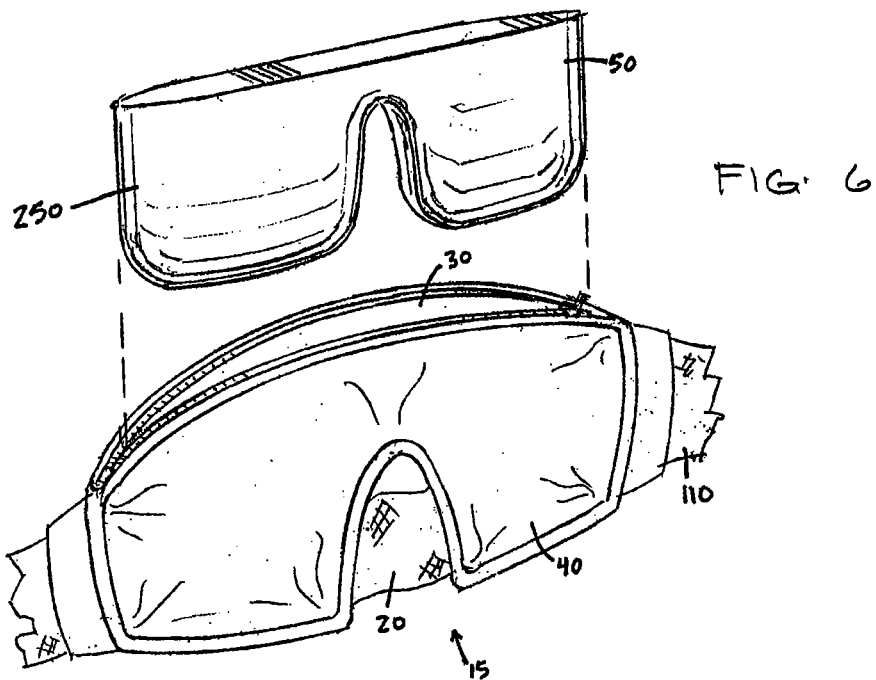
FIG. 6 is a perspective view of a therapy pad and a removable thermal insert in accordance with the present invention.

The embodiment of therapy pad 10 shown in FIGS. 1 and 2 includes at least one thermal unit 50 which is permanently enclosed within therapy pad 10. However, therapy pad 10 may designed such that thermal unit 50 is a removable insert 250, as shown in FIG. 6. Removable inserts 250 provide distinct advantages over permanent thermal units 50. If thermal units 50 are one-time use only, the use of removable inserts 250 prevents the user from having to dispose of therapy pad 10 entirely after only a single use. Furthermore, removable inserts 250 may be removed once they have reached ambient temperature and new inserts 250 may be added to bring therapy pad 10 back to a hot or cold temperature. In addition, the use of removable inserts 250 allows therapy pad 10 to be used for providing contrast therapy, which is highly recommended by today's medical professionals. For instance, the user may use a hot insert 250 for twenty minutes and then switch it with a cold insert 250 for an additional twenty minutes and repeat as necessary.

Figure 7:
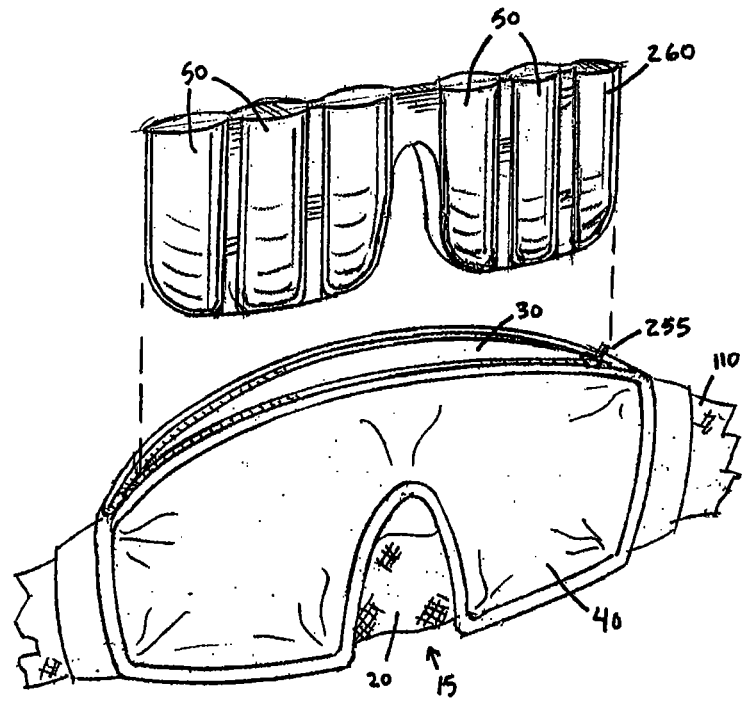
FIG. 7 is a perspective view of a therapy pad with an alternative removable thermal insert.

FIG. 6 shows a therapy pad 10 with a thermal unit 50 that is a removable insert 250. Therapy pad 10 may be opened such that inner layer 30 and outer layer 40 are separated. Removable insert 250 is placed inside therapy pad 10 in between inner layer 30 and outer layer 40. Therapy pad 10 may also include a means for closing the therapy pad 10. The closing device 255 can be made of Velcro®, buttons, snaps, a zipper or other types of fastening or closing elements. The embodiment shown in FIG. 6 includes a zipper as closing device 255 located along one side of therapy pad 10. Closing device 255 may be closed when removable insert 250 is placed within therapy pad 10 so that it cannot fall out. Another embodiment of therapy pad 10, shown in FIG. 7, includes removable insert 260 including a plurality of thermal units 50 separated from one another. This embodiment provides a more flexible therapy pad 10, especially in cases where thermal unit 50 is a rigid solid.

Figure 11:
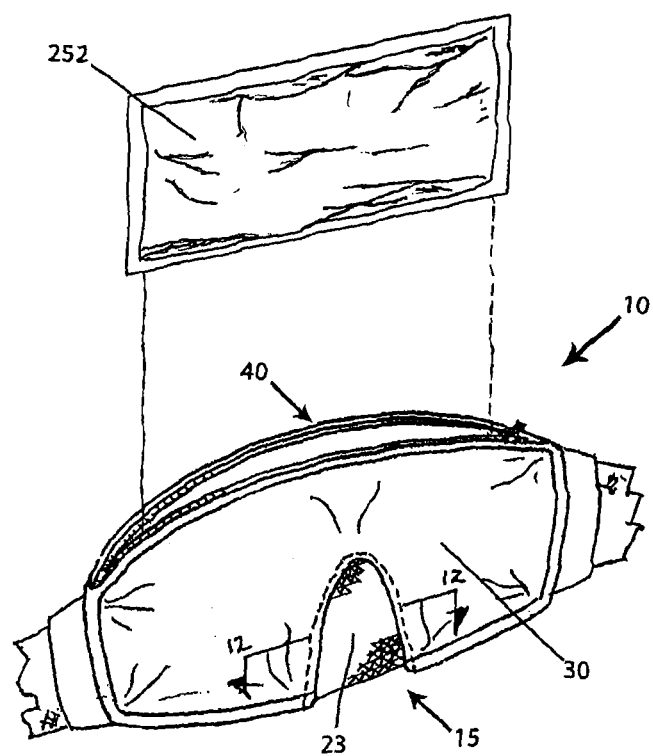
FIG. 11 is a perspective view of an alternative embodiment of a therapy pad and a removable thermal insert in accordance with the present invention.
Figure 12:
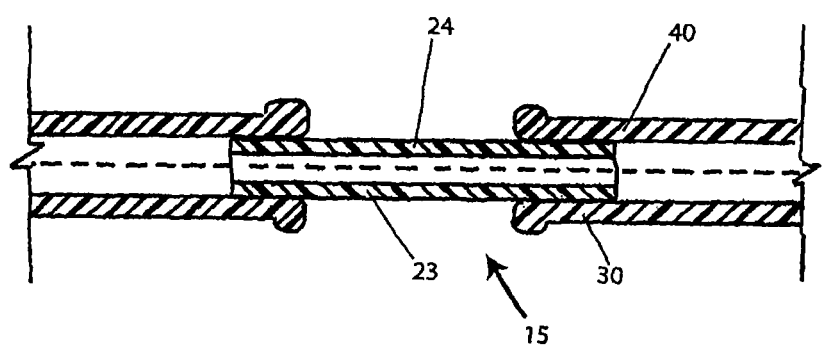
FIG. 12 is a cross-section view of the therapy pad shown in FIG. 11 taken along line 12-12.

Another embodiment of therapy pad 10 using a removable insert includes two flexible members 23 and 24 spanning slot 15 formed in each of inner layer 30 and outer layer 40 as shown in FIGS. 11 and 12. Removable insert 252 may be inserted between the side formed by flexible member 23 and inner layer 30 and the side formed by flexible member 24 and outer layer 40. This embodiment prevents the need for a removable insert 252 with a cutout section adapted for slot 15. Thus, the removable insert may be rectangular or oval.

Figure 8:
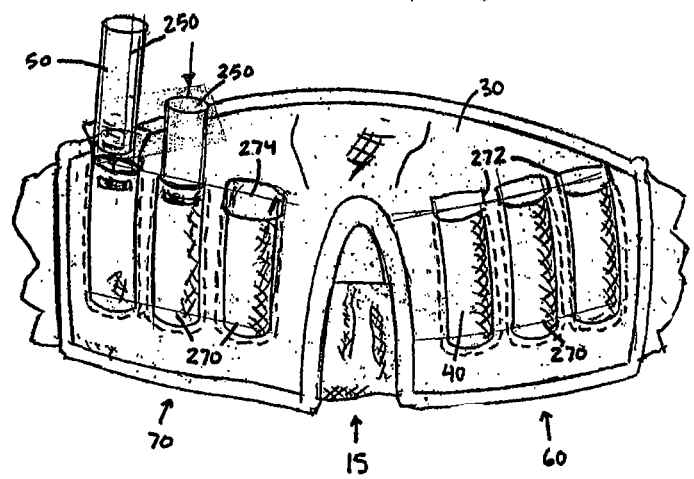
FIG. 8 is a front view of a therapy pad including pockets for removable thermal inserts.

Another embodiment of therapy pad 10, as shown in FIG. 8, includes at least one pocket 270 to hold removable insert 250 or 260. Pocket 270 is preferably located on an outer surface of therapy pad 10. In this embodiment outer layer 40 may consist of only the pocket 270 and is not required to cover the entire therapy pad 10. Pocket 270 may be closable, such that removable insert 250 or 260 does not fall out of pocket 270. An attachment member may be included to hold an open end 272 of pocket 270 closed. Alternatively, as shown in FIG. 8, a flap 274 may be provided to cover open end 272.

Thermal units 50 of therapy pad 10 may be formed of a material which heats up when exposed to air. Certain mixtures of natural chemicals undergo an exothermic reaction when mixed with oxygen. Thermal unit 50 may be formed by any of such mixtures to provide a therapy pad 10 which produces long lasting heat. Thermal units 50 using these chemicals are one-time use only. For this reason, therapy pads employing this type of thermal unit 50 may be disposable or may include one of insert 250 or 260 which may or may not be disposable.

Another embodiment includes thermal units 50 having a high specific heat capacity. High specific heat capacity thermal units 50 may be designed to be hot, cold or both hot and cold. Before using therapy pad 10 the user may prepare the temperature of the thermal units 50. This may be done by a plurality of methods including microwaving thermal units 50 or placing them in hot water to make them hot or placing them in the refrigerator or freezer to make them cold. Advantages of high specific heat capacity thermal units 50 is that they are inexpensive, may be multi-use and they are especially well designed for contrast therapy.

Yet another embodiment of therapy pad 10 includes thermal units 50 which include two separate chemical mixtures. Typically one of the chemicals is contained within a breakable pouch. Before using therapy pad 10 the user breaks the pouch allowing the chemicals to mix. The mixing of the two chemicals results in one of an endothermic or an exothermic reaction making therapy pad 10 cold or hot, respectively. Thermal units 50 of this variety can be used only one time. Again, therapy pad 10 may be disposable or removable units 250 or 260 may be used and be disposable.

Another embodiment of therapy pad 10 may include more than one type of thermal unit 50. Therapy pad 10 may include electrical heating coil 200 as well as high specific heat capacity thermal unit 50. Upon activation, the heating coil 200 rises in temperature and begins heating the high specific heat capacity unit 50. Once the thermal units 50 have reached a substantially high temperature, the heating coils 200 may be turned off or the therapy pad 10 may be unplugged. The high specific heat capacity unit 50 retains the heat of the therapy pad 10 allowing it to remain in use after being disconnected from the power source.

Figure 9:
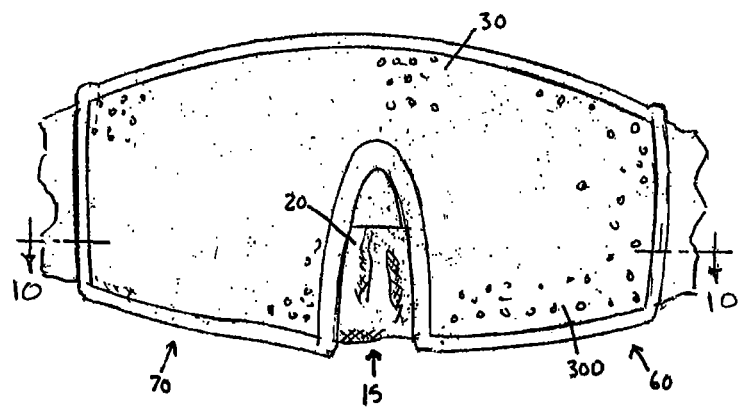
FIG. 9 is an alternative embodiment of the therapy pad in accordance with the present invention.
Figure 10:
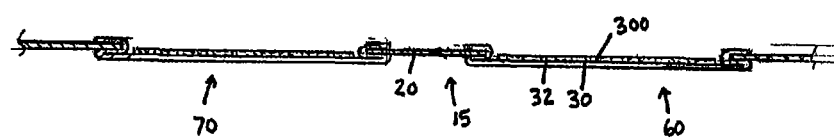
FIG. 10 is a cross-section view of the therapy pad shown in FIG. 9 taken along line 10-10.

A different embodiment of therapy pad 10 as shown in FIGS. 9 and 10 is pharmacological. Therapy pad 10 with therapeutic slot 15 includes a single outer layer 40 with an inner surface 32 coated with liquid or paste 300. Liquid 300 provides a sense of either heating or cooling using well known substances such as menthol or trolamine salicylate. Additionally, inner surface 32 can be porous to absorb liquid 300 and release specific quantities over time to allow for extended treatment. Alternatively, inner layer 30 can be porous and removable units placed inside therapy pad 10 can contain liquid 300 to be slowly dispensed through inner layer 30. The removable units may be formed of a sponge-like material to hold liquid 300. The therapy pad 10 with liquid 300 may also include adhesive 140 such that a strap or belt 110 is not required.

Although the preferred form of the invention has been shown and described, many features may be varied, as will readily be apparent to those skilled in this art. Thus, the foregoing description is illustrative and not limiting. It is the intention, therefore, to be limited only as indicated by the scope of the claims appended hereto.

We claim:

1. A temperature therapy pad comprising:
    a first layer;
    a second layer;
    an outer edge defined by at least a portion of one of the first and second layer;
    a slot extending inward from the outer edge, said slot substantially dividing the temperature therapy pad into first and second sections; and
    an electrical heating coil between the first and second layers for increasing a temperature of the temperature therapy pad; and
    an elastic member positioned in an opening created by the slot and generally extending from the first section to the second section.

2. The temperature therapy pad of claim 1 further comprising a strap for attaching the temperature therapy pad to a user.

3. The temperature therapy pad of claim 2 wherein the strap is elastic.

4. The temperature therapy pad of claim 1 wherein the temperature therapy pad is configured for use with a user's lower back.

5. The temperature therapy pad of claim 1 further comprising a controller for controlling the electrical heating coil.

6. The temperature therapy pad of claim 5 wherein the controller controls the temperature of the heating coil.

7. The temperature therapy pad of claim 5 wherein the controller determines a location where the heating coil is activated.

8. The temperature therapy pad of claim 1, wherein the slot extends at least half way across the temperature therapy pad.

9. A temperature therapy pad comprising:
    a first layer;
    a second layer;
    an outer edge defined by at least a portion of one of the first and second layer;
    a slot extending inward from the outer edge, said slot substantially dividing the temperature therapy pad into first and second sections;
    an electrical heating coil between the first and second layers for increasing a temperature of the temperature therapy pad; and
    an elastic member positioned in an opening created by the slot and generally extending from the first section to the second section.

10. The temperature therapy pad of claim 1, further comprising a middle section coupling the first section to the second section, wherein the electrical heating coil is configured to heat the first section and the second section but not the middle section.

* * * * *